United States Patent [19]

Mar et al.

[11] Patent Number: 5,226,260
[45] Date of Patent: Jul. 13, 1993

[54] METHOD FOR MANUFACTURING IMPLANTABLE CARDIAC DEFIBRILLATION LEADS UTILIZING A MATERIAL REMOVAL PROCESS

[75] Inventors: Craig Mar, Fremont; Benjamin D. Pless, Menlo Park, both of Calif.

[73] Assignee: Ventritex, Inc., Sunnyvale, Calif.

[21] Appl. No.: 819,106

[22] Filed: Jan. 9, 1992

[51] Int. Cl.$^5$ .............................................. B24C 1/00
[52] U.S. Cl. ........................................ 51/319; 51/320
[58] Field of Search ......................... 51/317, 319, 320

[56] References Cited

U.S. PATENT DOCUMENTS

| | | | |
|---|---|---|---|
| 3,636,623 | 1/1972 | Paine et al. | 51/320 |
| 4,291,707 | 9/1981 | Heilman et al. | |
| 4,631,250 | 12/1986 | Hayashi | 51/320 |
| 4,971,070 | 11/1990 | Holleman et al. | |
| 5,024,711 | 6/1991 | Gasser et al. | 51/320 |
| 5,083,402 | 1/1992 | Kirschner et al. | 51/320 |

*Primary Examiner*—M. Rachuba
*Attorney, Agent, or Firm*—Steven M. Mitchell; Mark J. Meltzer

[57] ABSTRACT

A method of manufacturing a medical electronic lead portion having an elastomeric mass and typically having a conductive metal member embedded in the elastomeric mass. The method includes the step of eroding elastomer of the mass from around the conductive metal member to form a predetermined shape by exposing the lead portion to a jet of gas containing entrained, particulate abrasive. Preferably, the particulate abrasive is softer than the conductive metal member to avoid scratching thereof. For example, soluble particulate abrasive such as sodium bicarbonate can be used.

2 Claims, 3 Drawing Sheets

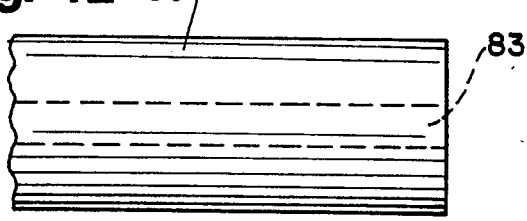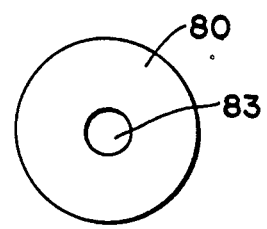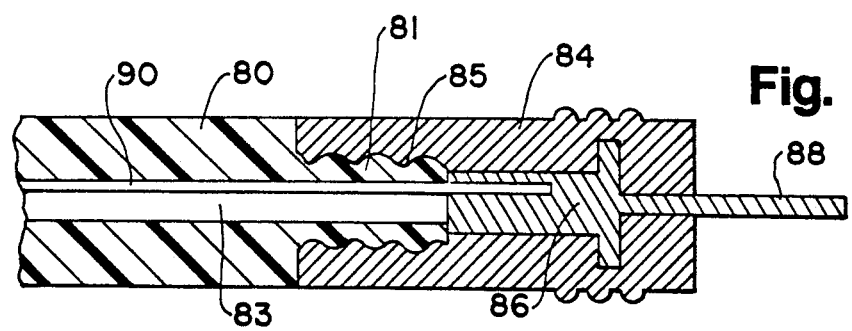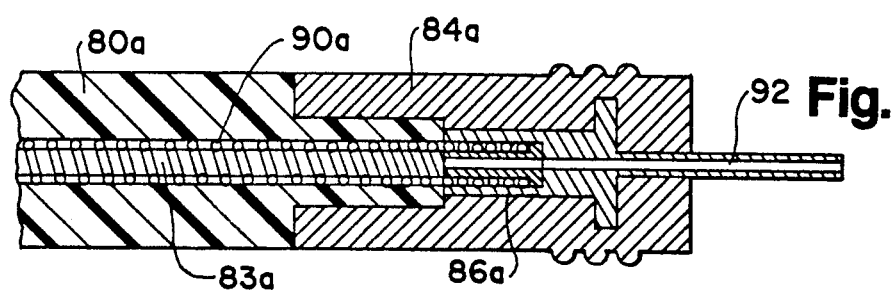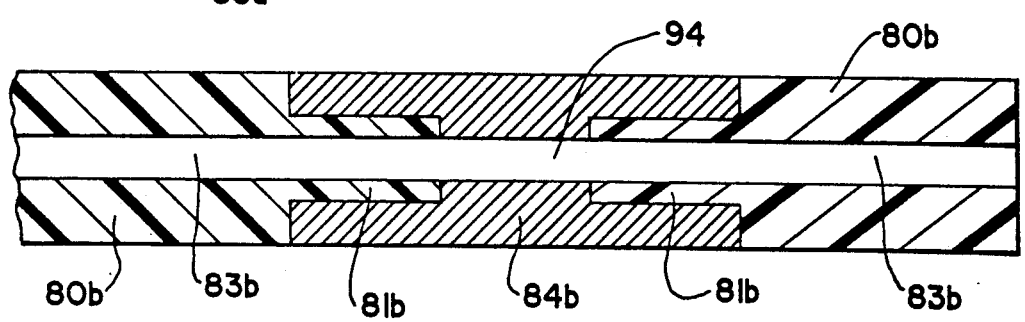

METHOD FOR MANUFACTURING IMPLANTABLE CARDIAC DEFIBRILLATION LEADS UTILIZING A MATERIAL REMOVAL PROCESS

BACKGROUND OF THE INVENTION

This invention relates to medical electrical stimulation electrodes in general and to implantable defibrillation electrodes in particular.

It is well known that cardiac arrhythmias may be controlled with devices such as implantable defibrillators. Past electrodes which deliver defibrillation therapy have been constructed of metal mesh adhered to a silicone rubber backing as disclosed in Heilman et al. in U.S. Pat. No. 4,291,707 or have been constructed of metal electrode coils adhesively bonded to a silicone rubber backing as disclosed in Holleman et al. in U.S. Pat. No. 4,971,070.

These electrodes have been manufactured using various techniques. In the case of the Heilman electrode, the electrode metal meth is either sandwiched between two layers of silicone rubber sheeting, one solid, and the other with open windows to allow for current distribution. In another embodiment of this electrode construction, the metal mesh is stitched onto the rubber sheeting. The problem with this manufacturing process is that the electrode is not firmly attached to the silicone rubber sheeting in all areas. Thus, tissue will have a tendency to grow into the electrode mesh and separate the electrode from the backing. If the need arises for explanting the electrode, complications arise due to the difficulty in separating the electrode from the ingrown tissue. In addition, the manufacturing methods are somewhat cumbersome to utilize.

In the case of the Holleman electrode, the electrode coils are adhesively bonded to the silicone sheeting either with or without a central silicone core being inserted into the coil. This technique involves an adhesive bonding step which must be carefully administered in order to ensure adequate bonding to all the surfaces. In addition, by using an adhesive, another material, which must be biocompatible, is added to the device tubs complicating matters.

It would be advantageous to have a process that would allow simple assembly and good control over the amount of exposed electrode and the amount of electrode adhesion to the insulative backing. This can be accomplished by completely embedding the electrode material in silicone or other elastomer, utilizing a molding operation. Then the electrode can be exposed via a material removal process. The problem with many material removal processes is that they are not easily controllable. If one were to try to machine, grind, or cut the electrode, there would be a high probability that the electrode material would be damaged in the process. In addition, rubber is a resilient material that is not readily amenable to some of the mentioned processes

SUMMARY OF THE INVENTION

This invention is directed to a new electrode fabrication technique which allows for the electrode material to be affixed to the insulative backing in a simple, reliable manner. The process is unique in that it can selectively remove some materials without damaging others. In this process the electrode material is first completely embedded in a rubber backing during a compression molding process. After the electrode is completely embedded in the rubber, selective areas and amounts of electrode can be exposed by utilizing the material removal process of this invention.

In a preferred process the removal means is accomplished by using a jet of compressed air carrying an abrasive to remove the rubber without damaging the electrode material. In the preferred embodiment, the abrasive process uses a non-toxic, water-soluble abrasive, softer than the electrode material, such as sodium bicarbonate, to erode the rubber away. The sodium bicarbonate does not harm the metals that comprise the electrode In addition the sodium bicarbonate is easy to clean off since it dissolves in water. The amount of material removed and the removal rate can be controlled by the blast pressure, orifice size of the delivery tool, and the distance from the material worked upon.

By selective partial removal of rubber from the electrode, one can maintain adhesion between the silicone rubber backing and the entire electrode surface at all points of electrode/rubber contact. This helps to prevent delamination of the electrode from the silicone, and limits the amount of tissue ingrowth. With less tissue ingrowth into the electrode material, the defibrillation lead is easier to explant at a later time.

This process can also be used in other areas of lead manufacture. Rework operations to remove excess rubber from other molding operations can be accomplished with this technique. Removal of material to allow for remolding operations is also possible. Removing material for molding or splicing similar or different dimension insulation tubing to other tubing or lead connectors is also possible.

BRIEF DESCRIPTION OF THE DRAWINGS

FIG. 12 shows a plan view of a portion of lead insulation tubing of constant inner and outer diameter;

FIG. 13 shows an end elevation of the lead insulation tubing of FIG. 12;

FIG. 14 is a plan view, taken partly in section, showing how the lead insulation tubing of FIG. 2 may be abraded to form a tip of less diameter, and how a connector of similar outer dimension has been molded or placed on to it;

FIG. 15 is a plan view, partly in section, of another embodiment similar to FIG. 14, where the tube of FIG. 12 may be abraded to form a tip, and a connector applied over the tip, in which connector has a hollow, tubular terminal pin; and FIG. 16 is an elevational view in which the abraded ends of two tubes similar to FIG. 12 may be connected with a molded connector.

DESCRIPTION OF SPECIFIC EMBODIMENTS

Figure 1:
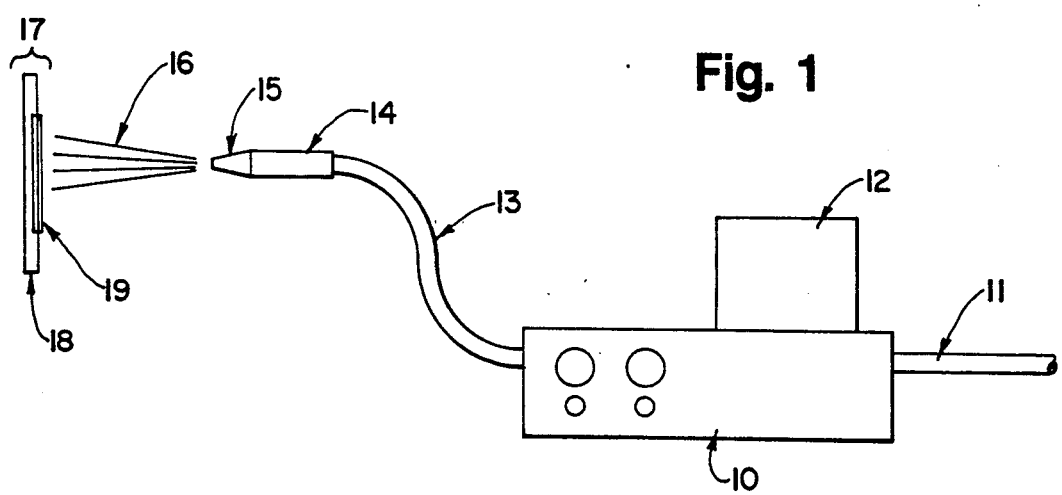
FIG. 1 shows a diagrammatic, plan view of the equipment used and the set up for practice of the material removal process.

FIG. 1 shows a plan view of the equipment used and the set up for the material removal process. The abrasive blasting machine 10, is connected to a pressurized gas supply via an incoming pressure line 11. The abrasive medium is stored in a receptacle 12, on the top of the machine. The abrasive medium is mixed into the pressurized air stream and fed out through another air line 13, to the hand held delivery tool 14. The mixture of air and abrasive medium is released through a hardened orifice 15, and an abrasive jet 16, is formed which can be directed to the part 17. In this drawing the part is composed of the silicone rubber backing 18, which has been partially eroded away to reveal the electrode material 19.

In the preferred process the pressure used is typically 80 psi. However, the pressures may change depending on the rate of removal required. The typical orifice used was a 0.046" diameter round opening. Other round orifices can be used some going down to 0.010" in diameter or even slot type orifices depending on the type of erosion coverage required. The orifice is typically held 0.5" away from the material to be removed. This distance can be changed to control the rate and coverage area of material removal. The typical size of the sodium bicarbonate particle is 150 microns. Other materials such as ground polyethylene powder or ground nut shells can also be used. In on embodiment the equipment used is a Comco Inc. Microblaster.

Figure 2:
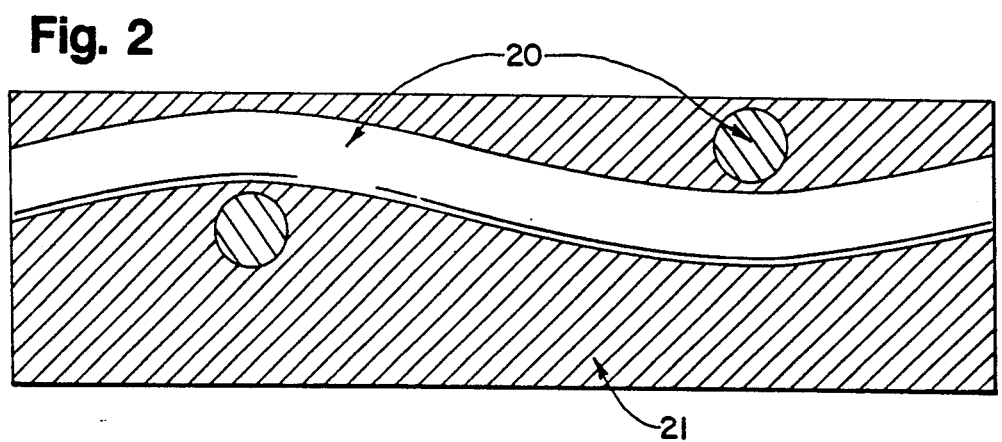
FIG. 2 shows an elevational view, partly in cross section, of a defibrillation mesh electrode after it has been completely embedded.
Figure 3:
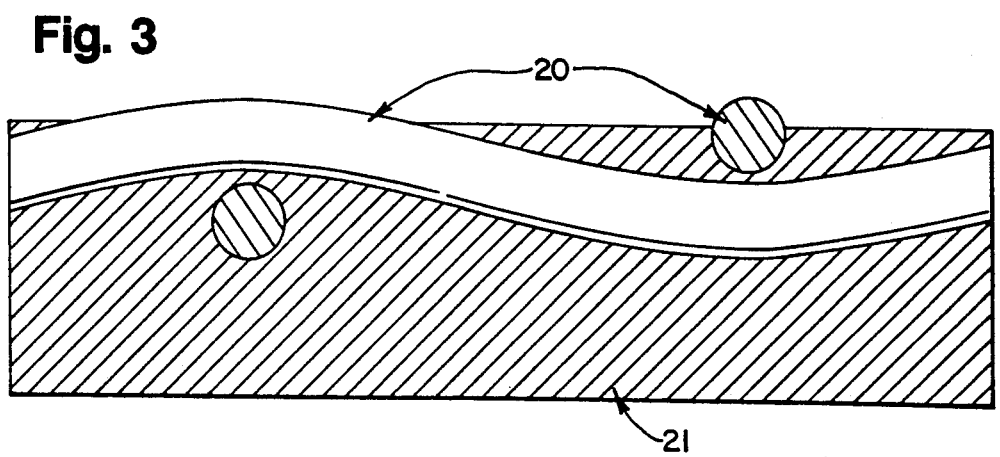
FIG. 3 shows an elevational view, partly in cross section, of the defibrillation mesh electrode of FIG. 2 after the silicone backing has been partially removed.

Typically, it is preferred for the abrasive particles used to be of a relatively soft material so as not to scratch the metal electrode material, while being hard enough to abrade silicone rubber backing 18, so that the structure as shown in FIG. 2, through abrasion by a pressurized air stream, can turn into a structure similar to that of FIG. 3. If desired, other water soluble salts and the like can be used such as sugar, sodium acetate, sodium chloride, or the like. Aluminum oxide and other insoluble materials may be used as well.

As a substitute technique, the elastomeric coating may be abraded by another kind of abrading stream such as a laser or plasma beam or an abrasive stream, as in electrical discharge machining or the like. It is generally preferred for biocompatible abrasives to be used so that any residue of abrasive that remains will not contribute to tissue reaction.

FIG. 2 shows a cross section of a defibrillation mesh electrode after it has been completely embedded in a silicone rubber wall 21 of a tubular lead or a flat patch of a lead. The mesh 20, is completely embedded in the rubber backing 21, from a compression molding process. The mesh may be made, for example, of an alloy of 90% titanium, 6% aluminum, and 4% vanadium, by weight, or alternatively pure titanium.

FIG. 3 shows a cross section of a defibrillation mesh electrode after the removal process. The top portion of the rubber backing 21, has been removed from the abrasive blasting process to partially expose the mesh 20. In one embodiment the mesh is composed of wires, 0.004" in diameter. Thus to halfway expose the mesh, a 0.004" thick layer of rubber would be removed. However the amount and thickness of rubber removed can vary, depending on the desired amount of electrode exposure. It is important to note that the abrasive process, using a sodium bicarbonate medium in particular, allows for selective removal of silicone rubber without harming the metal electrode (as shown in the figure). It can also be seen that the mesh is attached at all the crosspoints in the mesh structure, thus ensuring that the electrode is firmly attached to the silicone rubber backing.

Figure 4:
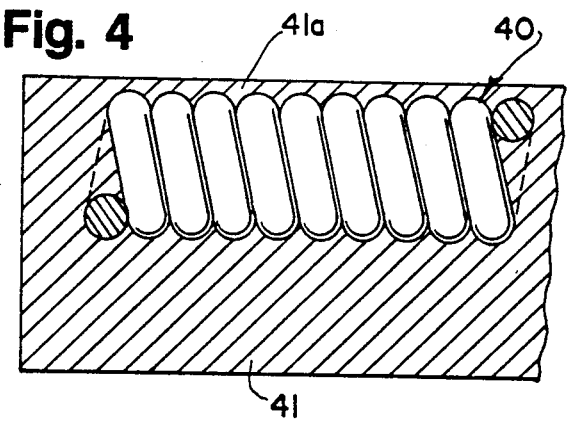
FIG. 4 shows an elevational view, partly in cross section, of a close wound defibrillation coil electrode after it has been completely embedded.
Figure 5:
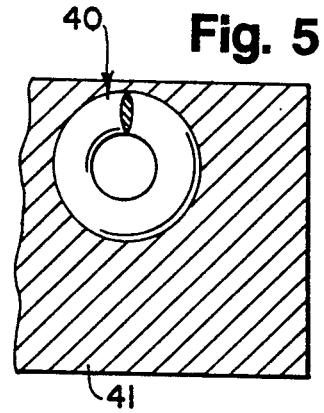
FIG. 5 is an end elevational view, partly in cross section, of FIG. 4.

FIGS. 4 and 5 show a cross section of a close wound defibrillation coil electrode after it has been completely embedded in a flat patch. The coil 40, is completely encapsulated in the rubber backing 41, from the compression molding process, and may be made, for example, of platinum, or an alloy of 90% platinum and 10% iridium, by weight.

Note that due to the close wound structure of the coil only the radially outermost portion of the coil may be adhered to the silicone rubber backing.

Figure 6:
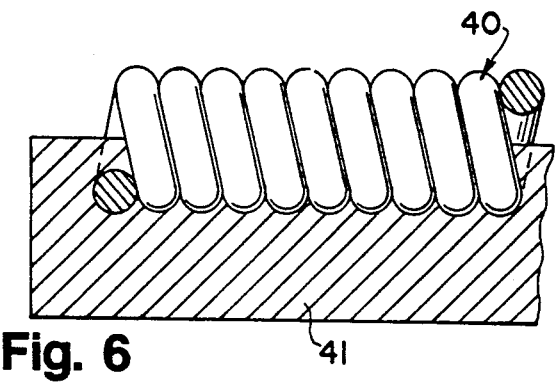
FIG. 6 shows an elevational view, partly in cross section, of the same portion of defibrillation coil electrode of FIG. 4 after the silicone backing has been partially removed.
Figure 7:
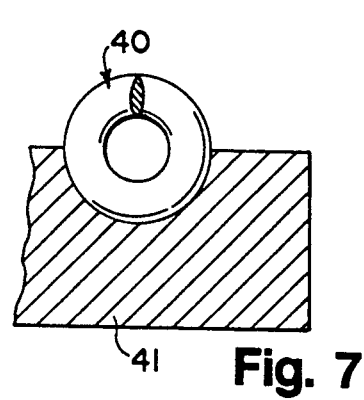
FIG. 7 is an end elevational view, taken partly in section, of FIG. 6.

FIGS. 6 and 7 show a cross section of the close wound defibrillation coil electrode of FIGS. 4 and 5 after the removal process. The top portion 41a of the rubber backing 41 has been removed by the abrasive blasting process to partially expose the coil 40. Note that due to the close wound structure of the coil only the radially outermost portion of the coil is typically adhered to the silicone rubber backing. Upon such partial rubber removal, the inner portions of the coil are exposed to the body and body fluids seeping through the coils, thus allowing greater surface area to deliver electrical current. In the one embodiment of the process the coil is composed of 0.003" diameter wire wound to form a 0.012" diameter coil. To expose the coil halfway, a 0.006" thick layer of rubber would be removed. However, the amount and thickness of rubber removed can vary, depending on the desired amount of electrode exposure. Note that even though some of the rubber is eroded away, the bottom portions of the coil are still completely embedded in the rubber, thus ensuring that there will be good adhesion between the coil and the rubber backing.

Figure 8:
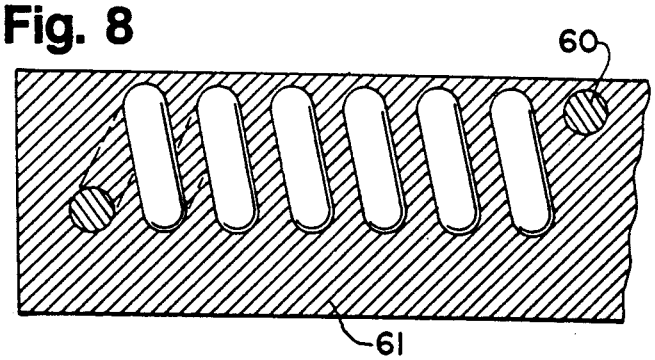
FIG. 8 shows an elevational view, partly in cross section, of a space wound defibrillation coil electrode after it has been completely embedded.
Figure 9:
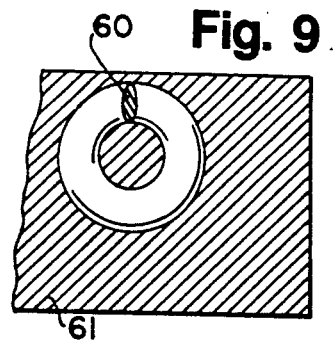
FIG. 9 is an end elevational view, taken partly in section, of FIG. 8.

FIGS. 8 and 9 show the space-wound defibrillation coil electrode after it has been completely embedded. The coil 60 is completely embedded in the rubber backing 61, from the compression molding process. Note that due to the space-wound structure of the coil, the interior and exterior portions of the coil are adhered to the silicone rubber backing.

Figure 10:
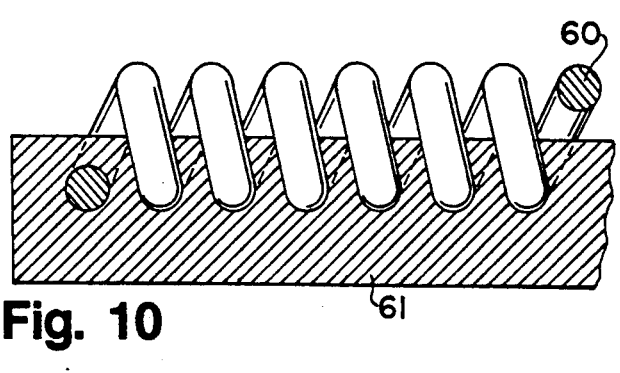
FIG. 10 shows an elevational view, partly in cross section, of the space wound defibrillation coil electrode of FIG. 8 after the silicone backing has been partially removed.
Figure 11:
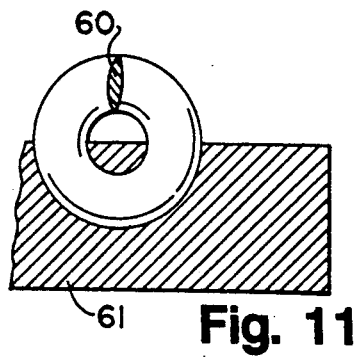
FIG. 11 is an end elevational view, taken partly in section, of FIG. 10.

FIGS. 10 and 11 show the space-wound defibrillation coil electrode after the removal process. The top portion of the rubber backing 61 has been removed from the abrasive blasting process to partially expose the coil 60. Note that the bottom portion of the coil is still completely embedded in the silicone rubber backing. This ensures excellent adhesion to the silicone for the life of the device. The amount of coil embedded in rubber and the amount of coil exposed can be varied between the conditions shown in FIG. 8 and FIG. 10, thus allowing excellent control over the electrode/rubber adhesion and amount of surface area for current delivery.

FIG. 12 shows a plan view of lead insulation tubing 80, of typically constant inner and outer diameter. In one embodiment this tubing has an inner diameter of 0.030" and an outer diameter of 0.125" and is typically composed of silicone rubber.

FIG. 13 shows a cross section of the lead insulation tubing 80 having a lumen 83, and being of typically constant inner and outer diameter shown in FIG. 12.

FIG. 14 shows a plan view of lead insulation tubing 80, after one end has had material removed by the process of this invention to form a reduced-diameter section 81. The length of reduced diameter section 81 can vary depending with bonding requirements to other structures. In one embodiment the length is 0.250" long. The configuration of material removal can be a step as shown here, or can gradually taper depending on other requirements. Section 81 may have an outer surface having ridges or other irregularities 85 to promote adhesion of connector member 84.

Lead insulation tubing 80 may be sealed as shown to connector member 84, which may be formed by insert molding on the end portion 81 of tubing 80, or may a separately-formed piece, as desired. The two members 80, 84 may be sealed together in any desired manner. Also, connector member 84 carries a conductive terminal pin 86, having an outwardly projecting terminal 88 as shown for electrical connection of the lead tubing with another terminal. Lead tubing 80 may carry a conductor 90, extending through the bore 83 thereof, and electrically connected to terminal pin 86 so that a conductive lead is provided.

Turning to FIG. 15, lead insulation tubing 80a is shown to be connected to a connector 84a, each of lead 80a and connector 84a being of similar design to the previous embodiment. Terminal 86a is provided, being similar in structure and purpose to the previous terminal 86 except for the presence of a lumen 92 extending from end to end thereof. Lead wire 90a is provided as in the previous embodiment, being connected with terminal pin 86a. Thus, the lead of FIG. 15 provides both electrical contact through terminal pin 86a, but also fluid communication can be provided through the lead due to the presence of lumen 92 of terminal pin 86a, which communicates with bore 83a of the lead.

Referring to FIG. 16, a pair of lead insulation tubings 80b, each having a bore 83b and carrying a tip section 81b which has been processed in accordance with this invention, are held in opposite ends of a connector 84b, which has a bore proportioned to receive the two tubings 80b to provide a joined lead tubing assembly having a common lumen as shown. A lead wire may be inserted through this elongated assembly of lead insulation tubings and connector 84b. Alternatively, the assembly may be used to convey fluids and the like.

Typically, each of connectors 84, 84a, 84b may be insert molded into its shown position, by which a spontaneous adhesion of the respective parts may be provided. While the diameter of each of connectors 84, 84a, 84b is shown to be the same as the diameter of the respective lead insulation tubings 80, 80a, 80b, variations in their respective diameters may be provided as desired, either with a step at the junction of the two diameters, or with a conically tapered transition area.

The above has been offered for illustrative purposes only, and is not intended to limit the scope of the invention of this application, which is as defined in the claims below.

Claim:

1. A method of manufacturing an implantable cardiac electrode partially embedded in an elastomeric material comprising the steps of:
   encapsulating a metal electrode in an elastomeric material; and
   directing a jet of abrasive material at said encapsulated electrode until a portion of said elastomeric material is removed to expose a portion of said metal electrode whereby an unexposed portion of said electrode is embedded in a backing of elastomeric material.

2. A method of manufacturing a tubular implantable medical lead comprising the steps of:
   encapsulating a conductive wire in a tubular elastomeric insulator material having a first outer diameter; and
   directing a jet of abrasive material at one end of said insulator material to remove a portion of said insulator material and thereby reduce the outer diameter of said portion to less than said first outer diameter.

* * * * *